US011540992B2

(12) United States Patent
Michitsuji et al.

(10) Patent No.: US 11,540,992 B2
(45) Date of Patent: Jan. 3, 2023

(54) PROCESS AND COMPOSITION FOR COLORING KERATIN FIBERS

(71) Applicant: L'OREAL, Paris (FR)

(72) Inventors: Tomotaka Michitsuji, Kawasaki (JP); Celine Bossard, Saint-Ouen (FR); Dhimoy Roy, Woodmead (ZA); Maxime De Boni, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/271,129

(22) PCT Filed: Aug. 13, 2019

(86) PCT No.: PCT/JP2019/032210
§ 371 (c)(1),
(2) Date: Feb. 24, 2021

(87) PCT Pub. No.: WO2020/045136
PCT Pub. Date: Mar. 5, 2020

(65) Prior Publication Data
US 2021/0369581 A1      Dec. 2, 2021

(30) Foreign Application Priority Data

Aug. 29, 2018 (JP) .............................. JP2018-160120

(51) Int. Cl.
*A61Q 5/10* (2006.01)
*A61K 8/46* (2006.01)
*A45D 19/00* (2006.01)
*A61K 8/44* (2006.01)
*A61Q 5/06* (2006.01)

(52) U.S. Cl.
CPC .......... *A61K 8/466* (2013.01); *A45D 19/0066* (2021.01); *A61K 8/44* (2013.01); *A61K 8/447* (2013.01); *A61Q 5/06* (2013.01); *A61Q 5/10* (2013.01); *A45D 2200/15* (2013.01); *A61K 2800/4324* (2013.01)

(58) Field of Classification Search
CPC ............ A61Q 5/10; A61Q 5/065; A61Q 5/06; A61K 2800/4324; A61K 8/41; A61K 8/466; A61K 8/447

USPC .......................................................... 132/208
See application file for complete search history.

(56) References Cited

U.S. PATENT DOCUMENTS

| | | | |
|---|---|---|---|
| 4,459,284 A | 7/1984 | Azuma et al. | |
| 7,413,579 B2* | 8/2008 | Seiler | A61Q 5/10 8/405 |
| 2009/0126755 A1* | 5/2009 | Guerin | A61Q 5/065 8/405 |
| 2010/0037909 A1* | 2/2010 | Gross | A61K 8/4953 8/409 |

FOREIGN PATENT DOCUMENTS

| | | |
|---|---|---|
| CN | 108289813 A | 7/2018 |
| CN | 108348786 A | 7/2018 |
| JP | 2017-039682 A | 2/2017 |
| WO | 2014/020146 A2 | 2/2014 |
| WO | 2015/198923 A1 | 12/2015 |
| WO | 2016/182086 A1 | 11/2016 |
| WO | WO 2016/182086 A1 * | 11/2016 ............... A61Q 5/04 |

OTHER PUBLICATIONS

STIC Search Report dated Mar. 14, 2022.*
International Search Report and Written Opinion for counterpart Application No. PCT/JP2019/032210, dated Nov. 18, 2019.
Translation of Chinese Office Action for counterpart Application No. 201980055695.4, dated Sep. 20, 2022.

* cited by examiner

*Primary Examiner* — Eisa B Elhilo
(74) *Attorney, Agent, or Firm* — The Marbury Law Group, PLLC

(57) ABSTRACT

The present invention relates to a process for coloring keratin fibers, preferably hair, comprising the steps of: (i) applying onto the keratin fibers a composition comprising (a) at least one compound chosen from alkylaminosulfonic acids and those of the formula (I) and (II), (b) at least one direct dye, and (c) at least one alkaline agent; (ii) heating the keratin fibers; and (iii) optionally rinsing and/or drying the keratin fibers. The present invention can provide superior coloring efficiency, such as color intensity and color lastingness.

16 Claims, No Drawings

PROCESS AND COMPOSITION FOR COLORING KERATIN FIBERS

CROSS REFERENCE TO RELATED APPLICATION

This is a national stage application of PCT/JP2019/032210, filed internationally on Aug. 13, 2019, which claims priority to Japanese Application No. 2018-160120, filed on Aug. 29, 2018, both of which are incorporated by reference herein in their entireties.

TECHNICAL FIELD

The present invention relates to a process, in particular a coloring process, for keratin fibers such as hair, and a composition used in the process.

BACKGROUND ART

It is known to dye keratin fibers, in particular human hair, with dyeing compositions containing oxidative coloring precursors, generally called oxidative bases, such as ortho- or para-phenylenediamines, ortho- or para-aminophenols and heterocyclic compounds. These oxidative bases are generally combined with couplers. These bases and these couplers are colorless or weakly colored compounds which, combined with oxidizing products, can give rise to colored compounds through an oxidative condensation process.

This type of coloring by oxidation makes it possible to obtain colors with very high visibility, and the ability to cover white hair and in a wide variety of shades but it results in damage to the keratin fibers due to the use of oxidizing agents and alkaline agents (in particular by repeated application or by combination with other hair treatments).

On the other hand, it is also known to dye keratin fibers, in particular human hair, with dyeing compositions containing direct dyes. Conventional direct dyes are in particular the following: benzene nitrates, anthraquinones, nitropyridines, azos, xanthenes, acridines, azines, and triarylmethane type or natural colorings. Hair coloring using direct dyes has advantages over hair coloring using oxidative dyes: it rarely gives rise to allergy issues, it causes less damage to the hair, and it gives vivid color visibility.

For example, JP-A-2017-39682 discloses compositions for dyeing hair including direct dyes.

DISCLOSURE OF INVENTION

An objective of the present invention is to provide a new process for coloring keratin fibers, such as hair, which can provide keratin fibers with improved color intensity and color lastingness using a direct dye.

The above objective of the present invention can be achieved by a process for coloring keratin fibers, preferably hair, comprising the steps of:
(i) applying onto the keratin fibers a composition comprising:
  (a) at least one compound chosen from alkylaminosulfonic acids and those of the following formula (I) and (II):

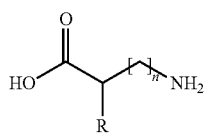
(I)

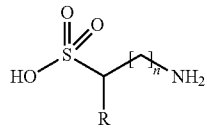
(II)

in which in formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
(b) at least one direct dye, and
(c) at least one alkaline agent,
(ii) heating the keratin fibers; and
(iii) optionally rinsing and/or drying the keratin fibers.

The process may be intended for coloring and reshaping keratin fibers, preferably hair.

The (a) compound may be selected from the group consisting of alkylaminosulfonic acids such as 2-(cyclohexylamino)ethanesulfonic acid; amino acids such as glycine, alanine, glutamic acid, aspartic acid, phenylalanine, β-alanine, isoleucine, leucine, proline, glutamine, serinze, threonine, valine, tryptophan, and tyrosine; oligomers of amino acids such as glycylglycine; aminosulfonic acids such as taurine; and mixtures thereof.

The (a) compound may be selected from the group consisting of 2-(cyclohexylamino)ethanesulfonic acid, glycine, alanine, taurine, and mixtures thereof.

The amount of the (a) compound in the composition may be from 1% to 30% by weight, preferably from 3 to 20% by weight, and more preferably from more than 5 to 15% by weight, relative to the total weight of the composition.

The (b) direct dye may comprise basic direct dye and neutral direct dye.

The amount of the (b) direct dye in the composition may be from 0.01% to 25% by weight, preferably from 0.1 to 15% by weight, and more preferably 0.1 to 8% by weight, relative to the total weight of the composition.

The amount of the (c) alkaline agent in the composition may be from 0.01% to 20% by weight, preferably from 0.1% to 15% by weight, more preferably from 1% to 10% by weight, and even more preferably from 2% to 8% by weight, relative to the total weight of the composition.

The composition may further comprise at least one organic acid salt of alkaline earth metal.

In the process according to the present invention, the keratin fibers may be heated during the heating step to from 50° C. to 180° C., preferably from 60° C. to 150° C., and more preferably from 70° C. to 120° C.

In the process according to the present invention, the composition may be the only active composition used in the process.

The pH of the composition may be 8.0 to 12.0, preferably from 8.5 to 11.5, and more preferably from 9.0 to 11.0.

The present invention also relates to a composition for coloring keratin fibers, preferably hair, by heating, comprising:

(a) at least one compound chosen from alkylaminosulfonic acids and those of the following formula (I) and (II):

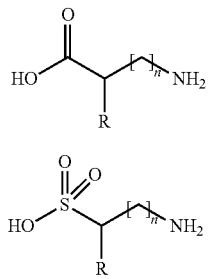

in which in formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
(b) at least one direct dye, and
(c) at least one alkaline agent.

The present invention also relates to a composition for coloring and reshaping keratin fibers, preferably hair, by heating, comprising:
(a) at least one compound chosen from alkylaminosulfonic acids and those of the following formula (I) and (II):

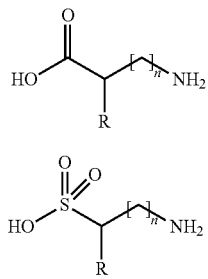

in which in formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
(b) at least one direct dye, and
(c) at least one alkaline agent.

The process and composition according to the present invention can be used to color keratin fibers, preferably hair, and can provide the keratin fibers with improved color intensity and color lastingness.

Also, the present invention can provide good usability such as short processing time due to one-time operation comprising the steps (i) to (iii) above.

In addition, the process and composition according to the present invention can be used to reshape or deform keratin fibers, preferably hair, and can provide the keratin fibers with sufficient reshaping efficiency such as strong wave intensity, at the same time as to color keratin fibers.

Therefore, the process and composition according to the present invention can be used to both of color and reshape or deform keratin fibers simultaneously in a significantly efficient manner due to the one-time operation, and can provide the keratin fibers with improved color intensity, color lastingness, and sufficient reshaping.

BEST MODE FOR CARRYING OUT THE INVENTION

After diligent research, the inventors have surprisingly found that the process according to the present invention can enhance the coloring efficiency, such as color intensity and color lastingness.

Thus, one aspect of the present invention is a process for coloring keratin fibers, preferably hair, comprising the steps of:
(i) applying onto the keratin fibers a composition comprising:
  (a) at least one compound chosen from alkylaminosulfonic acids and those of the following formula (I) and (II):

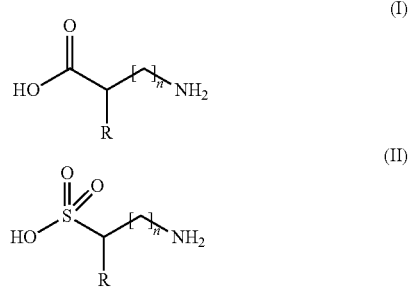

in which in formulae (I) and (II)
  R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
  (b) at least one direct dye, and
  (c) at least one alkaline agent,
(ii) heating the keratin fibers; and
(iii) optionally rinsing and/or drying the keratin fibers.

Furthermore, the inventors have surprisingly found that the use of the composition of the present invention can provide the keratin fibers with sufficient reshaping efficiency such as curl intensity, as well as the said coloring efficiency.

Therefore, the process can be intended for both of coloring and reshaping keratin fibers, preferably hair.

Accordingly, another aspect of the present invention is a process for coloring and reshaping keratin fibers, preferably hair, comprising the steps of:
(i) applying onto the keratin fibers a composition comprising:
  (a) at least one compound chosen from alkylaminosulfonic acids and those of the following formula (I) and (II):

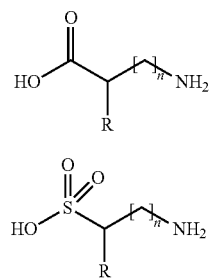

in which in formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
  (b) at least one direct dye, and
  (c) at least one alkaline agent,
(ii) heating the keratin fibers; and
(iii) optionally rinsing and/or drying the keratin fibers.

In addition, other aspects of the present invention are compositions which are used for the processes of the present invention above.

Hereafter, the process and the composition according to the present invention will each be described in a detailed manner.

[Process]

The process according to the present invention is a process for reshaping keratin fibers, preferably hair, comprising the steps of:
(i) applying onto the keratin fibers a composition comprising:
  (a) at least one compound chosen from alkylaminosulfonic acids and those of the following formula (I) and (II):

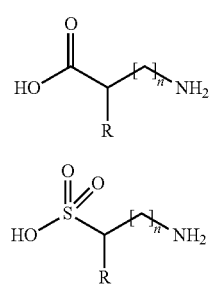

in which in formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium,
  (b) at least one direct dye, and
  (c) at least one alkaline agent,
(ii) heating the keratin fibers; and
(iii) optionally rinsing and/or drying the keratin fibers.

The details of the composition used in the process according to the present invention will be explained in the section titled [Composition] below. Thus, the composition used in the process according to the present invention can be the same as the composition according to the present invention.

The process according to the present invention is intended for coloring keratin fibers such as hair, with direct dyes. Preferably, only one type of the composition is used in the process according to the present invention.

In step (i), the composition which will be described later is applied to the keratin fibers. The application of the composition may be performed by any means, such as a brush and a comb. It may be possible that the keratin fibers after the application of the composition be left as they are for a certain amount of time typically from 10 seconds to 1 hour, preferably from 1 to 10 minutes, if necessary, in order to let the composition penetrates into the keratin fibers.

In step (ii), the keratin fibers are heated.

It may be preferable that the keratin fibers are heated during the (ii) heating step to 50° C. or higher, preferably 60° C. or higher, and more preferably 70° C. or higher.

It may be preferable that the keratin fibers are heated during the (ii) heating step to 180° C. or lower, preferably 150° C. or lower, and more preferably 120° C. or lower.

It may be preferable that the keratin fibers are heated during the (ii) heating step to from 50° C. to 180° C., preferably from 60° C. to 150° C., and more preferably from 70° C. to 120° C. The heating time may be, for example, from 1 to 30 minutes, and preferably from 5 to 20 minutes. The (ii) heating step can be performed by any heating means which can be controlled to realize the temperature desired for the process.

In one embodiment of the present invention, keratin fibers such as hair may be subjected to mechanical tension, which is typically used for deforming keratin fibers, before and/or after step (i), and preferably before step (ii), in order to reshape or deform keratin fibers, preferably temporary or permanent waving, and more preferably permanent waving, of keratin fibers such as hair.

Therefore, the process of the present invention can provide the process for coloring and reshaping or deforming keratin fibers at the same time and can provide the keratin fibers with improved color intensity, color lastingness, and sufficient reshaping.

The mechanical tension can be applied to the keratin fibers by any means to deform the keratin fibers to an intended shape. For example, the mechanical tension may be provided by at least one reshaping means selected from the group consisting of a curler, a roller, and a clip. The reshaping means may comprise at least one heater. If the keratin fibers are rolled around a curler, this rolling-up may be performed on the entire length of the keratin fibers or, for example, on half the length of the keratin fibers. Depending on, for example, the desired hairstyle shape and amount of curls, the rolling-up may be performed with more or less thick locks.

It may be preferable that the process according to the present invention comprise the step of placing the keratin fibers, before the (ii) heating step, in an occlusive space surrounding the keratin fibers to keep the keratin fibers wet. If the above deforming step of applying the mechanical tension to the keratin fibers is performed, this placing step can be performed after the deforming step.

The occlusive space may be formed by at least one coating means. The coating means may be rigid or flexible. The coating means may comprise at least one member selected from the group consisting of a film and a sheet. The material of the film or the sheet is not limited. For example, the film or the sheet may comprise a thermoplastic or thermosetting resin, a paper, a textile, a bonnet, a metal foil such as aluminum foil, and the like.

For example, the film or sheet may be set on a heating rod, a heating bar or a heating plate which is covered by keratin fibers, in order to form the occlusive space.

The occlusive space can restrict the evaporation of evaporable components such as water in the composition which has been applied to keratin fibers, and therefore, the temperature of the keratin fibers can be increased higher than that obtainable by a conventional heating process or device for the keratin fibers in open conditions. Furthermore, the keratin fibers can be heated effectively, and the keratin fibers can be heated evenly.

The occlusive space may form a condensation cage in which water and a component or components in the composition used in the process according to the present invention may evaporate from the keratin fibers, adhering to the wall of the coating means, and dropping onto the keratin fibers. This cycle may be repeated during the heating of the keratin fibers. Thus, the keratin fibers can always be kept wet, therefore drying out and deterioration of the keratin fibers can be prevented.

The formation of the occlusive space may be preferable because the keratin fibers in the occlusive space can be kept wet and the temperature of the keratin fibers can be kept constant. The wet conditions of the keratin fibers may be preferable for the ingredients in the composition used in the process according to the present invention to effectively penetrate into the keratin fibers.

In step (iii), the keratin fibers may be rinsed preferably with water, and/or may be dried. The drying of the keratin fibers can be performed with a conventional drying means such as a hair drier.

The process of the present invention can be used to not only color but also reshape or deform keratin fibers simultaneously with one-time operation comprising steps (i) to (iii) above, preferably including use of one type of composition as an only active composition. The expression "one-time operation" here means a series of steps for coloring, reshape, or deforming keratin fibers, including only one step application of an active composition to the keratin fibers.

[Composition]

The composition according to the present invention comprises:

(a) at least one compound chosen from alkylaminosulfonic acids and those of the following formula (I) and (II):

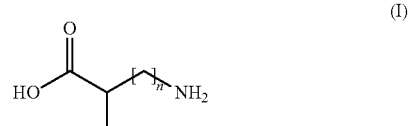

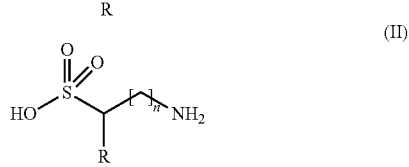

in which in formulae (I) and (II)

R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing, a cationic counterion such as an alkali metal, alkaline-earth metal, or ammonium, (b) at least one direct dye, and
(c) at least one alkaline agent.

It is preferable that the above composition be a cosmetic composition, in particular for coloring keratin fibers. It is preferable that the keratin fibers be hair.

The composition can be the only active composition for the process according to the present invention. In other word, the process according to the present invention may not need to use another active composition.

(Compound)

The composition according to the present invention comprises (a) at least one compound chosen from alkylaminosulfonic acids and those of the above formula (I) and (II). Two or more of the (a) compounds may be used in combination. Thus, a single type of the (a) compound or a combination of different types of the (a) compounds may be used.

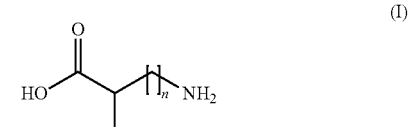

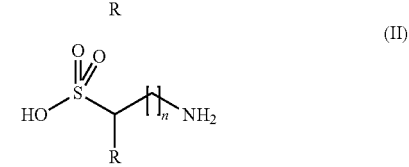

The alkylaminosulfonic acid may preferably have a $C_1$-$C_{20}$ alkyl group, preferably $C_5$-$C_{16}$ cycloalkyl group, and more preferably a $C_6$-$C_{12}$ cycloalkyl group, bonded to an imino group (—NH—) and a sulfonic acid moiety. The alkylaminosulfonic acid may be selected from the group consisting of 4-(2-hydroxyethyl)-1-piperazineethanesulfonic acid, 2-(cyclohexylamino)ethanesulfonic acid, and mixtures thereof.

The (a) compound(s) of the above formula (I) and (II) may be in their non-ionized form (I) or (II) or in their ionized or betaine form (I') or (II'):

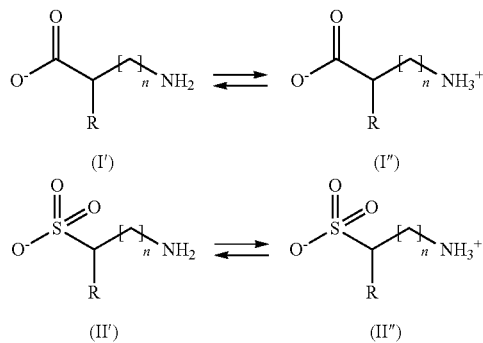

wherein

R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium, and n is 0 or 1.

As the $C_1$-$C_5$ alkyl group, mention may be made of a methyl group, an ethyl group, a propyl group, an isopropyl group, an n-butyl group, a sec-butyl group, an iso-butyl group, a tert-butyl group and a pentyl group. A methyl group and an ethyl group are preferable, and a methyl group is more preferable.

As the amino group, mention may be made of —NH$_2$, a group including —NH$_2$ such as a sulfonylamino group, and a group including —NH—R' (wherein R' denotes a hydroxyl group or a $C_1$-$C_5$ alkyl group as mentioned above) such as a hydroxyamino group and a $C_1$-$C_5$ alkylamino group. It should be noted that the term "amino" group here does not mean a part of a urea group. As the amino group, —NH$_2$ is preferable.

As the $C_6$-$C_{18}$ aromatic group, mention may be made of a monovalent $C_6$-$C_{18}$ aryl group such as a phenyl group and a substituted phenyl group such as a hydroxyphenyl group and an aminophenyl group, and a monovalent $C_7$-$C_{18}$ aralkyl group such as a tolyl group.

As the heterocyclic group, mention may be made of a monovalent, saturated or unsaturated, substituted or unsubstituted heterocyclic group, such as a substituted or unsubstituted pyrrolyl group, a substituted or unsubstituted pyrrolidinyl group, a substituted or unsubstituted pyridyl group, a substituted or unsubstituted piperidino group, a substituted or unsubstituted piperidinyl group, a substituted or unsubstituted morpholino group, a substituted or unsubstituted morpholinyl group, a substituted or unsubstituted furyl group, and a substituted or unsubstituted indolyl group such as 3-indolyl group.

The (a) compounds of the above formula (I) and (II) correspond to amino acids and aminosulfonic acids, respectively.

The (a) compound(s) is (are) preferably chosen from "neutral" or "acidic" amino acids or aminosulfonic acids. The term "neutral" is intended to mean amino acids or aminosulfonic acids which have a pH, at ambient temperature (25° C.), in water of inclusively between 5 and 7. The term "acidic" is intended to mean amino or aminosulfonic acids which have a pH, at ambient temperature, in water of less than 6.

The amino acids or aminosulfonic acids may comprise a number of amino groups less than or equal to the number of acid groups.

The (a) compound(s) may be selected from the group consisting of alkylaminosulfonic acids such as 2-(cyclohexylamino)ethanesulfonic acid; amino acids such as glycine, alanine, glutamic acid, aspartic acid, phenylalanine, β-alanine, isoleucine, leucine, proline, glutamine, serine, threonine, valine, tryptophan, and tyrosine; oligomers of amino acids such as glycylglycine; aminosulfonic acids such as taurine; and mixtures thereof.

It is preferable that the (a) compound be selected from a group consisting of 2-(cyclohexylamino)ethanesulfonic acid, glycine, alanine, taurine, and mixtures thereof.

The composition according to the present invention may contain the (a) compound(s) in an amount of 1% by weight or more, preferably 3% by weight or more, and more preferably 5% by weight or more, relative to the total weight of the composition.

The composition according to the present invention may contain the (a) compound (s) in an amount of 30% by weight or less, preferably 20% by weight or less, and more preferably 15% by weight or less, relative to the total weight of the composition.

The composition according to the present invention may contain the (a) compound (s) in an amount of from 1% to 30% by weight, preferably from 3 to 20% by weight, and more preferably 5 to 15% by weight, relative to the total weight of the composition.

(Direct Dye)

The composition according to the present invention includes (b) at least one direct dye. Two or more direct dyes may be used in combination. Thus, a single type of direct dye or a combination of different types of direct dyes may be used.

A direct dye means a colored substance which does not require the use of an oxidizing agent in order to develop its color.

The direct dye may be a natural direct dye or a synthetic direct dye.

The expression "natural direct dye" is understood to mean any dye or dye precursor that is naturally occurring and is produced by extraction (and optionally by purification) from a plant matrix or an animal such as an insect, optionally in the presence of natural compounds such as ash or ammonia.

As natural direct dyes, mention may be made of quinone dyes (such as lawsone and juglone), alizarin, purpurin, laccaic acid, carminic acid, kermesic acid, purpurogallin, protocatechaldehyde, indigoids such as indigo, sorghum, isatin, betanin, curcuminoids (such as curcumin), spinulosin, various types of chlorophyll and chlorophyllin, hematoxylin, hematein, brazilein, brazilin, safflower dyes (such as carthamin), flavonoids (such as rutin, quercetin, catechin, epicatechin, morin, apigenidin, and sandalwood), anthocyans (such as apigeninidin and apigenin), carotenoids, tannins, orceins, santalins and cochineal carmine.

It is also possible to use extracts or decoctions containing natural direct dye(s), in particular henna-based extracts, curcuma longa extract, sorghum leaf-sheath extract, haematoxylon campechianum extract, green tea extract, pine bark extract, cocoa extract, and logwood extract.

It is preferable that the natural direct dye be chosen from the group consisting of curcuminoids, santalins, chlorophyllin, haematoxylin, haematein, brazilein, brazilin, sorghum, laccaic acid, lawsone, juglone, alizarin, purpurin, carminic acid, kermesic acid, purpurogallin, protocatechaldehyde, indigoids, isatin, spinulosin, apigenin, orcein, betanin, flavonoids, anthocyans, and extracts or decoctions containing these compounds.

Alternatively, the natural direct dyes may be preferably chosen, for example, from hydroxylated quinones, indigoids, hydroxyflavones, santalins A and B, isatin and its derivatives, and brasilin and its hydroxylated derivative.

The hydroxylated quinones are preferably benzoquinones, naphthoquinones, and mono- or polyhydroxylated anthraquinones which are optionally substituted with groups such as alkyl, alkoxy, alkenyl, chloro, phenyl, hydroxyalkyl and carboxyl.

The naphthoquinones are preferably lawsone, juglone, flaviolin, naphthazarin, naphthopurpurin, lapachol, plumbagin, chloroplumbagin, droserone, shikonin, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphthoquinone and 3-methoxy-5-hydroxy-1,4-naphthoquinone.

The benzoquinones are preferably spinulosin, atromentin, aurentioglyocladin, 2,5-dihydroxy-6-methylbenzoquinone, 2-hydroxy-3-methyl-6-methoxybenzoquinone, 2, 5-dihydroxy-3,6-diphenylbenzoquinone, 2,3-dimethyl-5-hydroxy-6-methoxybenzoquinone and 2,5-dihydroxy-6-isopropylbenzoquinone.

The anthraquinones are preferably alizarin, quinizarin, purpurin, carminic acid, chrysophanol, kermesic acid, rhein, aloe emodin, pseudopurpurin, quinizarincarboxylic acid, frangula emodin, 2-methylquinizarin, 1-hydroxyanthraquinone and 2-hydroxyanthraquinone.

The indigoids are preferably indigo, indirubin, isoindigo and Tyrian purple.

The hydroxyflavones are preferably quercetin and morin.

The expression "synthetic direct dye" is understood to mean any dye or dye precursor that is produced by chemical synthesis.

The direct dye can be selected from the group consisting of acidic (anionic) direct dyes, basic (cationic) direct dyes, neutral (nonionic) direct dyes.

Non-limiting examples of syntheticdyes include (non-ionic) neutral, anionic (acidic), and cationic (basic) dyes such as azo, methine, carbonyl, azine, nitro(hetero)aryl types or tri(hetero)arylmethane direct dyes, porphyrins and phthalocyanines, alone or as mixtures.

More particularly, the azo dyes comprise an —N═N— functional group, the two nitrogen atoms of which are not simultaneously involved in a ring. However, it is not ruled out for one of the two nitrogen atoms of the —N═N— sequence to be involved in a ring.

The dyes of the family of the methines are more particularly compounds comprising at least one sequence chosen from >C═C< and —N═C<, the two atoms of which are not simultaneously involved in a ring. However, it is specified that one of the nitrogen or carbon atoms of the sequences can be involved in a ring. More particularly, the dyes of this family result from compounds of the following types: true methine (comprising one or more of the above-mentioned —C═C— sequences); azomethine (comprising at least one or more —C═N— sequences) with, for example, the azacarbocyanines and their isomers, the diazacarbocyanines and their isomers, the tetraazacarbocyanines; mono- and diarylmethane; indoamines (or diphenylamines); indophenols; indoanilines.

As regards to the dyes of the family of the carbonyls, mention maybe-made, for example, of synthetic dyes chosen from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazoline, perinone, quinacridone, quinophthalone, naphthalimide, anthrapyrimidine, diketopyrrolopyrrole or coumarin dyes.

As regards to the dyes of the family of the cyclic azines, mention may in particular be made of azine, xanthene, thioxanthene, fluorindine, acridine, (di)oxazine, (di)thiazine or pyronine dyes.

The nitro(hetero)aromatic dyes are more particularly nitrobenzene or nitropyridine direct dyes.

As regards to the dyes of porphyrin or phthalocyanine type, use may be made of cationic or noncationic compounds optionally comprising one or more metals or metal ions, such as, for example, alkali and alkaline earth metals, zinc and silicon.

Mention may be made, as examples of synthetic direct dyes which are particularly suitable, of nitrobenzene dyes, azo, azomethine or methine direct dyes, azacarbocyanines, such as tetraazacarbocyanines (tetraazapentamethines), quinone and in particular anthraquinone, naphthoquinone or benzoquinone direct dyes, or azine, xanthene, triarylmethane, indoamine, phthalocyanine and porphyrin direct dyes, alone or as mixtures. More preferably still, these synthetic direct dyes are chosen from nitrobenzene dyes, azo, azomethine or methine direct dyes and tetraazacarbocyanines (tetraazapentamethines); alone or as mixtures.

Mention may be made, among the azo, azomethine, methine or tetraazapentamethine direct dyes which can be used according to the invention, of the cationic dyes described in Patent Applications WO 95/15144, WO 95/01772 and EP 714 954; FR 2 189 006, FR 2 285 851, FR-2 140 205, EP 1 378 544 and EP 1 674 073.

Thus, mention may in particular be made of the cationic direct dyes corresponding to the following formulae:

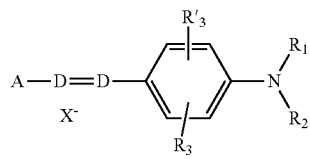

in which:

D represents a nitrogen atom or the —CH group, $R_1$ and $R_2$, which are identical or different, represent a hydrogen atom; a $C_1$-$C_4$ alkyl radical which can be substituted by a —CN, —OH or —NH$_2$ radical or can form, with a carbon atom of the benzene ring, an optionally oxygen-comprising or nitrogen-comprising heterocycle which can be substituted by one or more $C_1$-$C_4$ alkyl radicals; or a 4'-aminophenyl radical, $R_3$ and $R'_3$, which are identical or different, represent a hydrogen atom, a halogen atom chosen from chlorine, bromine, iodine and fluorine, a cyano radical, a $C_1$-$C_4$ alkyl radical, a $C_1$-$C_4$ alkoxy radical or an acetyloxy radical, $X^-$ represents an anion, preferably chosen from chloride, methyl sulphate and acetate, A represents a group chosen from the following structures:

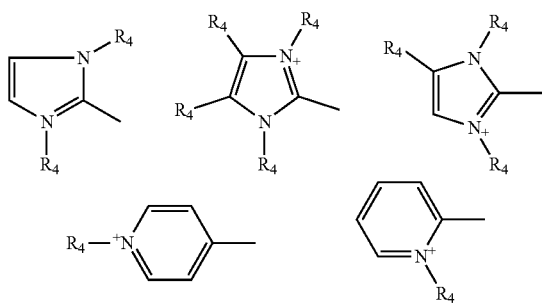

in which R$_4$ represents a C$_1$-C$_4$ alkyl radical which can be substituted by a hydroxyl radical;

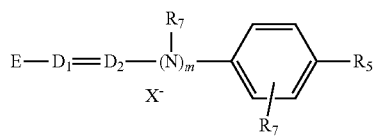

in which:

R$_5$ represents a hydrogen atom, a C$_1$-C$_4$ alkoxy radical or a halogen atom, such as bromine, chlorine, iodine or fluorine, R$_6$ represents a hydrogen atom or a C$_1$-C$_4$ alkyl radical or forms with a carbon atom in the benzene ring, a heterocycle which optionally comprises oxygen and/or is optionally substituted by one or more C$_1$-C$_4$ alkyl groups, R$_7$ represents a hydrogen atom or a halogen atom, such as bromine, chlorine, iodine or fluorine, D$_1$ and D$_2$, which are identical or different, represent a nitrogen atom or the —CH group, m=0 or 1, X$^-$ represents a cosmetically acceptable anion preferably chosen from chloride, methyl sulphate and acetate, E represents a group chosen from the following structures:

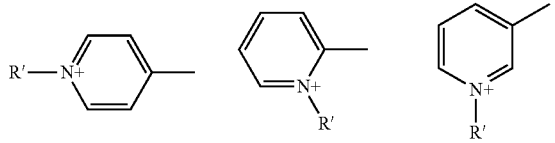

in which R' represents a C$_1$-C$_4$ alkyl radical;

when m=0 and when D$_1$ represents a nitrogen atom, then E can also denote a group with the following structure:

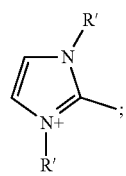

in which R' represents a C$_1$-C$_4$ alkyl radical.

The synthetic direct dye may be selected from fluorescent dyes. Two or more types of fluorescent dyes may be used in combination.

The use of some fluorescent dyes may make it possible to obtain, on dark hair, colors which are more visible than with conventional hydrophilic or hydrophobic direct dyes. Furthermore, these fluorescent dyes, when applied to dark hair, may also make it possible to lighten the hair without damaging it.

As used herein, the term "fluorescent dyes" is understood to mean fluorescent compounds and optical brighteners. In at least one embodiment, the fluorescent dye is soluble in the medium of the composition.

Fluorescent dyes are fluorescent compounds which absorb visible radiation, for example, wavelengths ranging from 400 to 800 nm, and which are capable of re-emitting light in the visible region at a higher wavelength.

According to one embodiment, the fluorescent dyes useful for the present invention re-emit orange-colored fluorescent light. They exhibit, for instance, a maximum re-emission wavelength ranging from 500 to 700 nm.

Non-limiting examples of fluorescent dyes include compounds known in the art, for example, those described in Ullmann's Encyclopedia of Industrial Chemistry, Release 2004, 7th edition, "Fluorescent Dyes" chapter.

The optical brighteners of the present disclosure, also known under the name of "brighteners", or "fluorescent brighteners", or "fluorescent brightening agents" or "FWA", or "fluorescent whitening agents", or "whiteners", or "fluorescent whiteners", are colorless transparent compounds as they do not absorb in visible light but only in ultraviolet light (wavelengths ranging from 200 to 400 nanometers) and convert the energy absorbed into fluorescent light of higher wavelength emitted in the visible part of the spectrum, generally in the blue and/or green, that is to say in wavelengths ranging from 400 to 550 nanometers.

Optical brighteners are known in the art, for example, they are described in Ullmann's Encyclopedia of Industrial Chemistry (2002), "Optical Brighteners" and Kirk-Othmer Encyclopedia of Chemical Technology (1995): "Fluorescent Whitening Agents".

The fluorescent dyes which can be used in the composition of the present disclosure include compounds known in the art, for example, those described in French Patent No. 2 830 189.

Soluble fluorescent compounds that may especially be mentioned include those belonging to the following families: naphthalimides, coumarins, xanthenes and in particular xanthenodiquinolizines and azaxanthenes; naphtholactams; azlactones; oxazines; thiazines; dioxazines; azo compounds; azomethines; methines; pyrazines; stilbenes; ketopyrroles; and pyrenes.

If present, the fluorescent dyes are preferred, more particularly, those re-emitting orange-colored fluorescent light.

In terms of ionic nature, the (b) direct dye may be selected from the group consisting of acidic direct dyes, basic direct dyes and neutral direct dyes, which covers all possible types of direct dyes, such as so-called nitro dyes and HC dyes. Acidic direct dyes have an anionic moiety in their chemical structure. Basic direct dyes have a cationic moiety in their chemical structure. Neutral direct dyes are nonionic.

According to an embodiment, it is preferable that the (b) direct dye comprises at least one acidic direct dye.

The anionic direct dyes are commonly known as "acidic direct dyes" for their affinity with alkaline substances (see, for example, "*Industrial Dyes, Chemistry, Properties, Application*", Klaus Hunger Ed. Wiley-VCH Verlag GmbH & Co KGaA, Weinheim 2003). Anionic or acid dyes are known in the literature (see, for example, "*Ullman's Encyclopedia of Industrial Chemistry*", Azo Dyes, 2005 Wiley-VCH Verlag GmbH & Co. KGaA, Weinheim 10.1002/14356007.a03 245, point 3.2; *ibid*, Textile Auxiliaries, 2002 Wiley-VCH Verlag GmbH & Co. KGaA, Weinheim 10.1002/14356007.a26 227 and "*Ashford's Dictionary of Industrial Chemicals*", Second Edition, p. 14-p. 39, 2001).

The term "anionic direct dyes" means any direct dye comprising in its structure at least one sulfonate group $SO_3^-$ and/or at least one carboxylate group $C(O)O^-$ and/or at least one phosphonate group $P(=O)O^-O^-$ and optionally one or more anionic groups $G^-$ with $G^-$, which may be identical or different, representing an anionic group chosen from alkoxide $O^-$, thioalkoxide $S^-$, phosphonate, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

The preferred anionic dyes of the formula of the invention are chosen from acidic nitro direct dyes, acidic azo dyes, acidic azine dyes, acidic triarylmethane dyes, acidic indoamine dyes, acidic anthraquinone dyes, anionic styryl dyes, and indigoids and acidic natural dyes; each of these dyes containing at least one sulfonate, phosphonate or carboxylate group bearing a cationic counterion $X^+$, where $X^+$ represents an organic or mineral cationic counter ion preferably chosen from alkali and alkaline-earth metals, such as $Na^+$ and $K^+$ Preferred acid dyes may be chosen from:

a) the diaryl anionic azo dyes of formula (II) or (II'):

R$_7$, R$_8$, R$_9$, R$_{10}$, R'$_7$, R'$_8$, R'$_9$ and R'$_{10}$, which may be identical or different, represent a hydrogen atom or a group chosen from:

alkyl;
alkoxy, alkylthio;
hydroxyl, mercapto;
nitro;
$R°—C(X)—X'—$, $R°—X'—C(X)—$, $R°—X'—C(X)—X"—$ with R° representing a hydrogen atom or an alkyl or aryl group; X, X' and X", which may be identical or different, representing an oxygen or sulfur atom, or NR with R representing a hydrogen atom or an alkyl group;
$(O)_2S(O^-)—$, $X^+$ as defined previously;
$(O)CO^-—$, $X^+$ as defined previously;
$(O)P(O_2^-)—$, $2X^+$ as defined previously;
$R"—S(O)_2—$, with R" representing a hydrogen atom or an alkyl, aryl, (di)(alkyl)amino or aryl(alkyl)amino group; preferably a phenylamino or phenyl group;
$R'"—S(O)_2—X'—$ with R'" representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)—$, $X^+$ and iv) alkoxy with $X^+$;
optionally substituted heteroaryl; preferably a benzothiazolyl group;
cycloalkyl; especially cyclohexyl,
Ar—N=N— with Ar representing an optionally substituted aryl group, preferably a phenyl optionally substituted with one or more alkyl, $(O)_2S(O^-)—$, $X^+$ or phenylamino groups;
or alternatively two contiguous groups R$_7$ with R$_8$ or R$_8$ with R$_9$ or R$_9$ with R$_{10}$ together form a fused benzo group A'; and R'$_7$ with R'$_8$ or R'$_8$ with R'$_9$ or R'$_9$ with R'$_{10}$ together form a fused benzo group B'; with A' and B' optionally substituted with one or more groups chosen from i) nitro; ii) nitroso; iii) $(O)_2S(O^-)—$, $X^+$; iv) hydroxyl; v) mercapto; vi) (di)(alkyl)amino; vii) $R°—C(X)—X'—$; viii) $R°—X'—C(X)—$; ix) $R°—X'—C(X)—X"—$; x) Ar—N=N— and xi) optionally substituted aryl(alkyl)amino; with $X^+$, R°, X, X', X" and Ar as defined previously;
W represents a sigma bond σ, an oxygen or sulfur atom, or a divalent radical i) —NR— with R as defined previously, or ii) methylene —C(R$_a$)(R$_b$)— with R$_a$ and R$_b$, which may be identical or different, representing a hydrogen atom or an aryl group, or alternatively R$_a$ and R$_b$ form, together with the carbon atom that

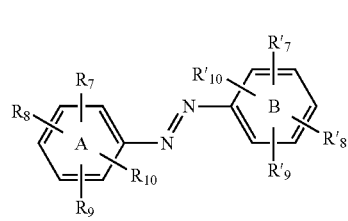

(II)

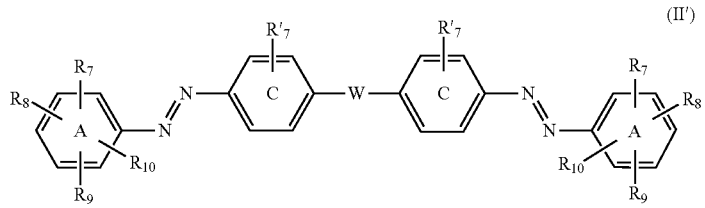

(II')

bears them, a spiro cycloalkyl; preferably W represents a sulfur atom or R$_a$ and R$_b$ together form a cyclohexyl;

it being understood that formulae (II) and (II') comprise at least one sulfonate $(O)_2S(O^-)—$, $X^+$ or phosphonate $(O)P(O_2^-)$ $2X^+$ or carboxylate $(O)C(O^-)—$, $X^+$ radical on one of the rings A, A', B, B' or C with $X^+$ as defined previously;

As examples of dyes of formula (II), mention may be made of Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Food Red 17, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Pigment Red 57; and as examples of dyes of formula (II'), mention may be made of Acid Red 111, Acid Red 134, Acid yellow 38;

b) the anthraquinone dyes of formulae (III) and (III'):

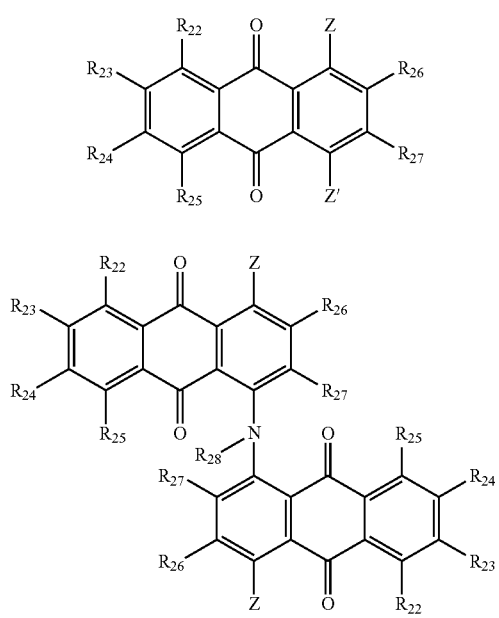

in which formulae (III) and (III'):
$R_{22}$, $R_{23}$, $R_{24}$, $R_{25}$, $R_{26}$ and $R_{27}$, which may be identical or different, represent a hydrogen or halogen atom or a group chosen from:
alkyl;
hydroxyl, mercapto;
alkoxy, alkylthio;
aryloxy or arylthio optionally substituted, preferably substituted with one or more groups chosen from alkyl and $(O)_2S(O^-)$—, $X^+$ with $X^+$ as defined previously;
aryl(alkyl)amino optionally substituted with one or more groups chosen from alkyl and $(O)_2S(O^-)$—, $X^+$ with $X^+$ as defined previously;
(di)(alkyl)amino;
(di)(hydroxyalkyl)amino;
$(O)_2S(O^-)$—, $X^+$ with $X^+$ as defined previously;
Z' represents a hydrogen atom or a group $NR_{28}R_{29}$ with $R_{28}$ and $R_{29}$, which may be identical or different, representing a hydrogen atom or a group chosen from:
alkyl;
polyhydroxyalkyl such as hydroxyethyl;
aryl optionally substituted with one or more groups, particularly i) alkyl such as methyl, n-dodecyl, n-butyl; ii) $(O)_2S(O^-)$—, $X^+$ with $X^+$ as defined previously; iii) $R^\circ$—C(X)—X'—, $R^\circ$—X'—C(X)—, $R^\circ$—X'—C(X)—X"— with $R^\circ$, X, X' and X" as defined previously, preferably $R^\circ$ represents an alkyl group;
cycloakyl; especially cyclohexyl;
Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;
it being understood that formulae (III) and (III') comprise at least one sulfonate group $(O)_2S(O^-)$—, $X^+$ with $X^+$ as defined previously;
As examples of dyes of formula (III), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT Violet 2, and as examples of dyes of formula (III'), mention may be made of Acid Black 48; and c) the quinoline-based dyes of formula (IV):

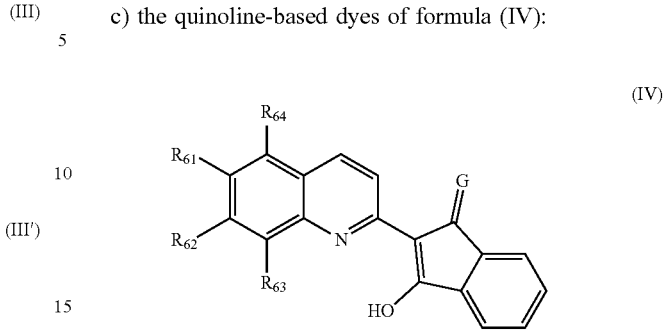

in which formula (IV):
$R_{61}$ represents a hydrogen or halogen atom or an alkyl group;
$R_{62}$, $R_{63}$ and $R_{64}$, which may be identical or different, represent a hydrogen atom or a group $(O)_2S(O^-)$—, $X^+$ with $X^+$ as defined previously;
or alternatively $R_{61}$ with $R_{62}$, or $R_{61}$ with $R_{64}$, together form a benzo group optionally substituted with one or more groups $(O)_2S(O^-)$—, $X^+$ with $X^+$ as-defined previously;
G represents an oxygen or sulfur atom or a group $NR_e$ with $R_e$ representing a hydrogen atom or an alkyl group; particularly G represents an oxygen atom;
it being understood that formula (IV) comprises at least one sulfonate group $(O)_2S(O^-)$—, $X^+$ with $X^+$ as defined previously;
As examples of dyes of formula (IV), mention may be made of Acid Yellow 2, Acid Yellow 3 and Acid Yellow 5.
It is preferable that the acidic direct dye be selected from the group consisting of Yellow 5, Orange 4, EXT. Violet 2, Acid Black 1 and Acid Violet 43 (CI 60730).
According to an embodiment, it is preferable that the (b) direct dye comprises at least one basic direct dye.
The basic direct dyes, which can be used in the present invention, can include, but are not limited to, Basic Blue3, Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Green 4, Basic Orange 1, Basic Orange 2, Basic Red 1, Basic Red 2, Basic Red 22, Basic Red 46, Basic Red 76, Basic Red 118, Basic Violet 1, Basic Violet 3, Basic Violet 4, Basic Violet 10, Basic Violet 11:1, Basic Violet 14, Basic Violet 16, Basic Yellow 11, Basic Yellow 28, and Basic Yellow 57.
According to an embodiment, it is preferable that the (b) direct dye comprises at least one neutral (nonionic) direct dyes.
The neutral (nonionic) direct dyes, which can be used in the present invention, can include, but are not limited to, nitro dyes, such as 4-amino-3-nitrophenol, 2-amino-5-nitrophenol, 2-nitro-5-glyceryl methylaniline, 3-methylamino-4-nitrophenoxyethanol, 4-hydroxypropylamino-3-nitrophenol, HC dyes such as HC Yellow 2, HC Yellow 4, HC Yellow 5, HC Yellow 9, Yellow 10, HC Red 1, HC Red 3, HC Red 7, HC Red 10, HC Red 11, HC Blue 2, HC Blue 12, HC Blue 14, HC Orange 1, HC Orange 2, HC Violet 1, HC Violet 2, and disperse dyes.
The examples of the disperse dyes may include, but are not limited to, Disperse Black 9, Disperse Blue 1, Disperse Blue 3, Disperse Blue 7, Disperse Brown 4, Disperse Orange 3, Disperse Red 11, Disperse Red 15, Disperse Red 17, Disperse Violet 1, Disperse Violet 4, and Disperse Violet 15.

In one particular embodiment of the present invention, the (b) direct dye comprises at least one basic direct dye and at least one neutral direct dye in combination. In another particular embodiment of the present invention, the (b) direct dye comprises two or more types of basic direct dyes in combination.

The amount of the basic direct dye may be 0.001% by weight or more, preferably 0.01% by weight or more, and may be 5% by weight or less, preferably 3% by weight or less, relative to the total weight of the composition.

In one particular embodiment of the present invention, the (b) direct dye comprises two or more types of neutral direct dyes in combination. In another particular embodiment of the present invention, the neutral direct dyes comprise nitro dyes, HC dyes, and disperse dyes in combination.

The amount of the neutral direct dye may be 0.01% by weight or more, preferably 0.1% by weight or more, more preferably 1% by weight or more, and may be 20% by weight or less, preferably 15% by weight or less, and more preferably 10% by weight or less, relative to the total weight of the composition.

In a certain embodiment of the present invention, the (b) direct dye does not comprise any acidic direct dye.

The composition according to the present invention may contain the (b) direct dye(s) in an amount of 0.01% by weight or more, preferably 0.1% by weight or more, and more preferably 1% by weight or more, relative to the total weight of the composition.

The composition according to the present invention may contain the (b) direct dye(s) in an amount of 25% by weight or less, preferably 15% by weight or less, and more preferably 8% by weight or less, relative to the total weight of the composition.

The composition according to the present invention may contain the (b) direct dye(s) in an amount of from 0.01% to 25% by weight, preferably from 0.1 to 15% by weight, and more preferably 0.1 to 8% by weight or 1 to 8% by weight, relative to the total weight of the composition.

(Alkaline Agent)

The composition according to the present invention may further comprise at least one (c) alkaline agent. Two or more (c) alkaline agents may be used in combination. Thus, a single type of alkaline agent or a combination of different types of alkaline agents may be used.

The (c) alkaline agent at a high temperature may cause lanthionization in keratin fibers which could contribute to reshaping of the keratin fibers.

The (c) alkaline agent may be an inorganic alkaline agent. It may be possible that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogenophosphate. However, it is preferable that the (c) alkaline agent not be ammonia because of the odor thereof. Thus, it is preferable that the inorganic alkaline agent be selected from inorganic ammonium salts such as ammonium carbonate and ammonium bicarbonate; and alkylammonium hydroxides such as tetramethylammonium hydroxide.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

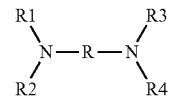

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The amount of the (c) alkaline agent(s) in the composition according to the present invention may be 0.01% by weight or more, preferably 0.1% by weight or more, more preferably 1% by weight or more, and even more preferably 2% by weight or more, relative to the total weight of the composition.

On the other hand, the amount of the (c) alkaline agent(s) in the composition according to the present invention may be 20% by weight or less, preferably 15% by weight or less, more preferably 10% by weight or less, and even more preferably 8% by weight or less, relative to the total weight of the composition.

The amount of the (c) alkaline agent(s) in the composition according to the present invention may range from 0.01% to 20% by weight, preferably from 0.1% to 15% by weight, more preferably from 1% to 10% by weight, and even more preferably from 2% to 8% by weight, relative to the total weight of the composition.

(Other Ingredients)

The composition according to the present invention may also comprise at least one additional ingredient.

The amount of the additional ingredient(s) is not limited, but may be from 0.1 to 10% by weight relative to the total weight of the composition according to the present invention. The additional ingredient(s) may be selected from the group consisting of organic solvents, in particular water-soluble organic solvents, oils; solid fatty substances, surfactants, hydrophilic thickeners; anionic, nonionic or amphoteric polymers; peptides and derivatives thereof; protein hydrolyzates; swelling agents and penetrating agents; agents for combating hair loss; anti-dandruff agents; associative-type or not, natural or synthetic thickeners for oils; suspending agents; sequestering agents; opacifying agents; dyes; sunscreen agents; vitamins or provitamins; fragrances; preserving agents, stabilizers; and mixtures thereof.

The composition according to the present invention typically comprises water.

The amount of water in the composition may be from 50 to 99% by weight, preferably from 55 to 95% by weight, and more preferably from 60 to 90% by weight, relative to the total weight of the composition.

Organic Acid Salt of Alkaline Earth Metal

The composition according to the present invention may further comprise at least one organic acid salt of alkaline earth metal. Two or more such salts may be used in combination. Thus, a single type of such salt or a combination of different types of such salts may be used.

If a plurality of organic acid salts of alkaline earth metal is used, it is possible that the type of organic acid is different and/or the type of alkaline earth metal is different.

The alkaline earth metal may be selected from magnesium and calcium.

The type of the organic acid is independent from the type of the organic acid forming the organic acid salt of alkaline earth metal. It is preferable that the organic acid is different from the organic acid forming the organic acid salt of alkaline earth metal.

The organic acid may be selected from α-hydroxy acids.

The a-hydroxy acids may be represented by the following formula (V):

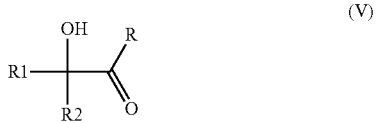

wherein

R1=H, —OH, —NH$_2$, —CH$_2$COOH or a linear or branched C$_{1-4}$ alkyl,

R2=H, —COOH, —CHOH—COOH, —CF$_3$, —CH=CH$_2$, —NHCONH$_2$, a linear, branched or cyclic C$_{1-8}$ alkyl optionally substituted with a radical chosen from —OH, Cl, —NH$_2$, —COOH, —CF$_3$ and —SCH$_3$; a phenyl or benzyl optionally substituted with one —OH or —OCH$_3$ radical; or alternatively the radical

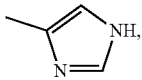

and

R1 and R2 may also together form an oxo radical (=O) or a cyclopropyl, cyclobutyl, hydroxycyclobutyl, cyclopentyl or cyclohexyl ring with the carbon atom that bears them, or alternatively the radical

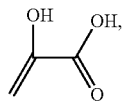

and when R1=H, R2 may also represent a —(CHOH)$_2$CH$_2$OH or —(CHOH)$_3$CH$_2$OH radical, R=—OH or —NR3R4 with R3, R4=H or a linear or branched C$_{1-4}$ alkyl optionally substituted with one or two OH radicals, as well as stereoisomers, organic or mineral salts and solvates thereof.

The α-hydroxy acids may be selected from the following: glycolic acid, oxalic acid, lactic acid, 1-hydroxy-1-cyclopropanecarboxylic acid, 2-hydroxy-3-butenoic acid, 2-hydroxyisobutyric acid, 2-hydroxy-n-butyric acid, isoserine, glyceric acid, 2-hydroxy-3-methylbutyric acid, 2-hydroxy-2-methylbutyric acid, 2-hydroxyvaleric acid, 4-amino-2-hydroxybutyric acid, 1-hydroxycyclohexanecarboxylic acid, dihydroxyfumaric acid, citramalic acid, tartaric acid, citric acid, 2-hydroxy-4-(methylthio)butyric acid, mandelic acid, 2-hydroxy-3-methylvaleric acid, glyoxylurea, β-imidazolelactic acid, 2-trifluoromethyl-2-hydroxypropionic acid, hexahydromandelic acid, 2-hydroxyoctanoic acid, arabic acid, 3-phenyllactic acid, hydroxyphenylglycine, 3-hydroxymandelic acid, 4-hydroxymandelic acid, 2-hydroxynonanoic acid, L-arginic acid, 3-methoxymandelic acid, 4-methoxymandelic acid, 3-(4-hydroxyphenyl)lactic acid, tartronic acid, β-chlorolactic acid, 1-cyclopentanol-1-carboxylic acid, 1,2-dihydroxycyclobutanecarboxylic acid, 2-ethyl-2-hydroxybutyric acid, α-hydroxyisocaproic acid, α-hydroxycaproic acid, 2-hydroxy-3,3-dimethylbutyric acid, malic acid, hydroxytartronic acid, gluconic acid, lactamide, N-methyllactamide, N-ethyllactamide, N,N-dimethyllactamide, N-2-hydroxyethyllactamide, and stereoisomers, organic or mineral salts and solvates thereof.

The α-hydroxy acid can be preferably selected from the group consisting of glycolic acid, oxalic acid, L-lactic acid, DL-lactic acid, D-lactic acid, malic acid, tartaric acid, DL-glyceric acid, arabic acid, gluconic acid, hydroxytartronic acid, lactamide, N-methyllactamide, N-ethyllactamide, and N-2-hydroxyethyllactamide, and more preferably selected from the group consisting of gluconic acid, glycolic acid, lactic acid, malic acid, citric acid, tartaric acid, and mandelic acid, and even more preferably the α-hydroxy acid is gluconic acid.

If gluconate is used as the organic acid salt of alkaline earth metal, in particular Mg, the time period of the heating step (ii) in the process according to the present invention can be shortened. Although not bound by any theory, it is believed that this effect is based on catalytic effects of the alkaline earth metal gluconate such as magnesium gluconate.

The amount of the organic acid salt(s) of alkaline earth metal in the composition according to the present invention may be 0.001% by weight or more, preferably 0.01% by weight or more, and more preferably more than 0.1% by weight, and be 5% by weight or less, preferably 3% by weight or less, and more preferably 1% by weight or less. relative to the total weight of the composition (pH)

The pH of the composition according to the present invention is 8.0 or higher, preferably 8.5 or higher, and more preferably 9.0 or higher.

The pH of the composition according to the present invention is 12.0 or lower, preferably 11.5 or lower, and more preferably 11.0 or lower.

The pH of the composition according to the present invention is 8.0 to 12.0, preferably from 8.5 to 11.5, and more preferably from 9.0 to 11.0.

[Use]

The present invention can also provide a cosmetic use of the composition comprising (a) at least one compound chosen from alkylaminosulfonic acids and those of the formula (I) and (II) as defined above, (b) at least one direct dye, and, (c) at least one alkaline agent, for coloring keratin fibers, such as hair.

The said cosmetic use according to the present invention can provide the keratin fibers with superior coloring efficiency, such as color intensity and color lastingness.

The present invention can also provide a cosmetic use of the composition comprising (a) at least one compound chosen from alkylaminosulfonic acids and those of the formula (I) and (II) as defined above, (b) at least one direct dye, and, (c) at least one alkaline agent, for coloring and reshaping or deforming keratin fibers, such as hair.

The cosmetic use according to the present invention can be performed in one-time operation. In addition, the composition used in the cosmetic use according to the present invention can be an only active composition for coloring keratin fibers or coloring and reshaping or deforming keratin fibers, such as hair.

The said cosmetic use of the composition of the present invention can provide the keratin fibers with sufficient reshaping efficiency such as curl intensity, as well as the said coloring efficiency.

EXAMPLES

The present invention will be described in a more detailed manner by way of examples. However, these examples should not be construed as limiting the scope of the present invention.

Example 1 and Comparative Example 1

{Preparations}
The following liquid compositions according to Example 1 and Comparative Example 1 shown in Table 1 were prepared by mixing the ingredients shown in Table 1. The numerical values for the amounts of the ingredients shown in Table 1 are all based on "% by weight" as active raw materials.

TABLE 1

|  | Ex. 1 | Comp. Ex. 1 |
|---|---|---|
| Sodium Hydroxide | 1.2 | — |
| Magnesium Gluconate | 0.25 | 0.25 |
| Ethanolamine | 1.22 | — |
| Taurine | 7.8 | — |
| Basic Brown 17 | 0.07 | 0.07 |
| 3-Methylamino-4-Nitrophenoxyethanol | 0.1 | 0.1 |
| Disperse Violet 1 | 0.042 | 0.042 |
| 2-Nitro-5-Glyceryl Methylaniline | 0.53 | 0.53 |
| HC Blue No. 2 | 1.4 | 1.4 |
| HC Violet No. 2 | 0.96 | 0.96 |
| HC Blue No. 14 | 0.26 | 0.26 |
| Water | qsp 100 | qsp 100 |
| pH | 10.5 | 7.3 |
| Delta E (Color Intensity at day of application) | 61.4 | 33.1 |
| Delta E (Color Lastingness (vs. day of application)) | 5.4 | 15.4 |
| Number of curl (Curling Efficacy) Wet hair | 5 | 2 |
| Dry hair | 5 | 2.5 |

{Evaluations}
(Coloring Procedure of Example)
3 g of composition according to Example 1 was applied on 1 g of a pre-shampooed Chinese 100% white hair swatch (20 cm) and Japanese natural hair swatch (20 cm). Each of hair swatches was wound onto a 20-mm perm rod (Ohiro digital perm machine ODIS-2) and covered by a physical wrap of a plastic film, and then heated by a digital perm machine for 10 minutes at 90° C. After the hair on rod was cooled at ambient temperature for 5 minutes, the physical wrap was removed, and the hair was then removed from the rod. The hair was then rinsed with tap water, and dried naturally overnight.

(Coloring Procedure of Comparative Example)
3 g of composition according to Comparative Example 1 was applied on 1 g of a pre-shampooed Chinese 100% white hair swatch (20 cm) and Japanese natural hair swatch (20 cm). Each of hair swatches was wound onto a 20-mm perm rod (Ohiro digital perm machine ODIS-2) and covered by a physical wrap of a plastic film, and then kept at ambient temperature for 15 minutes. After removing the physical wrap, the hair was then removed from the rod, rinsed with tap water, and then dried naturally overnight.

The color intensity, curl lastingness, and curl efficiency were evaluated as follows.
(Color Intensity)
The difference in color of the Chinese 100% white hair swatch before and after the above coloring procedure was measured by measuring the value of LAB (lightness/green-red/blue-yellow) with using Konica Minolta Spectrophotometer CM-3600A. 6 points of the hair swatch were evaluated in total. ΔE* (between the color of the uncolored original swatch and the color of the colored swatch under ΔL*a*b system) was calculated. The higher ΔE* is, the better the color intensity is.
(Color Lastingness)
The colored Chinese 100% white hair swatch was shampooed for 28 times. The difference in color of the colored Chinese 100% white hair swatch before and after shampooing for 28 times was measured by measuring the value of LAB (lightness/green-red/blue-yellow) with using Konica Minolta Spectrophotometer CM-3600A. 6 points of the hair swatch were evaluated in total. ΔE* (between the color of the colored swatch and the color of the shampooed swatch under ΔL*a*b system) was calculated. The smaller ΔE* is, the better the color lastingness is.
(Curling Efficacy)
The number of curls were counted for the colored Japanese natural hair swatch before and after drying the swatch.

The results are shown in Table 1.

As shown in Table 1, the process comprising an application of a composition including a combination of taurine, sodium hydroxide, and ethanol amine onto hair and heating the hair produced superior color intensity and color lastingness to the comparative process where the composition does not include the combination and the heating step is absent. In addition, the process according to the present invention also could significantly improve curling efficacy, which leads to superior reshaping or deforming efficacy of the keratin fibers.

The invention claimed is:
1. A process for coloring and reshaping keratin fibers comprising:
(i) applying onto the keratin fibers a composition comprising:
(a) at least one compound of formula (II):

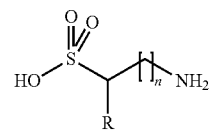

wherein in formula (II):
R is chosen from a hydrogen atom, or a linear or branched, $C_1$-$C_5$ alkyl group, and n is 0 or 1;
(b) at least one direct dye; and
(c) at least one alkaline agent;
(ii) heating the keratin fibers; and
(iii) optionally rinsing and/or drying the keratin fibers.
2. The process according to claim 1, wherein the keratin fibers are hair.

3. The process according to claim 1, wherein the (a) at least one compound is taurine.

4. The process according to claim 1, wherein the amount of the (a) at least one compound ranges from 1% to 30% by weight, relative to the total weight of the composition.

5. The process according to claim 1, wherein the amount of the (a) at least one compound ranges from 5% to 15% by weight, relative to the total weight of the composition.

6. The process according to claim 1, wherein the (b) at least at one direct dye is chosen from basic direct dyes and neutral direct dyes.

7. The process according to claim 1, wherein the (b) at least one direct dye is present in an amount ranging from 0.01% to 25% by weight, relative to the total weight of the composition.

8. The process according to claim 1, wherein the (b) at least one direct dye is present in an amount ranging from 0.1% to 15% by weight, relative to the total weight of the composition.

9. The process according to claim 1, wherein the (c) at least one alkaline agent is present in an amount ranging from 0.01% to 20% by weight, relative to the total weight of the composition.

10. The process according to claim 1, wherein the (c) at least one alkaline agent is present in an amount ranging from 1% to 10% by weight, relative to the total weight of the composition.

11. The process according to claim 1, wherein the composition further comprises at least one organic acid salt of alkaline earth metal.

12. The process according to claim 1, wherein the keratin fibers are heated, during the heating step, to a temperature ranging from 50° C. to 180° C.

13. The process according to claim 1, wherein the keratin fibers are heated, during the heating step, to a temperature ranging from 70° C. to 120° C.

14. The process according to claim 1, wherein the composition is the only active composition used in the process.

15. The process according to claim 1, wherein the pH of the composition ranges from 8.0 to 12.0.

16. A composition comprising:
(a) at least one compound chosen from alkylaminosulfonic acids and compounds of formula (II):

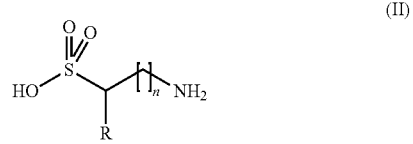

(II)

wherein in formula (II):
R is chosen from a hydrogen atom, or a linear or branched, $C_1$-$C_5$ alkyl group, and n is 0 or 1;
(b) at least one direct dye; and
(c) at least one alkaline agent.

* * * * *